(12) United States Patent
Chadha

(10) Patent No.: US 11,324,792 B2
(45) Date of Patent: May 10, 2022

(54) HERBAL PHARMACEUTICAL COMPOSITIONS FOR ANO-RECTAL DISEASES AND METHOD OF PREPARATION THEREOF

(71) Applicant: Kanwaldeep Singh Chadha, Uttar Pradesh (IN)

(72) Inventor: Kanwaldeep Singh Chadha, Uttar Pradesh (IN)

( * ) Notice: Subject to any disclaimer, the term of this patent is extended or adjusted under 35 U.S.C. 154(b) by 385 days.

(21) Appl. No.: 15/780,818

(22) PCT Filed: Dec. 2, 2016

(86) PCT No.: PCT/IB2016/057303
§ 371 (c)(1),
(2) Date: Jun. 1, 2018

(87) PCT Pub. No.: WO2017/093961
PCT Pub. Date: Jun. 8, 2017

(65) Prior Publication Data
US 2020/0254045 A1    Aug. 13, 2020

(30) Foreign Application Priority Data

Dec. 3, 2015 (IN) .......................... 3944/DEL/2015

(51) Int. Cl.
*A61K 36/328*    (2006.01)
*A61K 36/28*    (2006.01)
*A61K 36/744*    (2006.01)

(52) U.S. Cl.
CPC ............ *A61K 36/328* (2013.01); *A61K 36/28* (2013.01); *A61K 36/744* (2013.01)

(58) Field of Classification Search
None
See application file for complete search history.

(56) References Cited

U.S. PATENT DOCUMENTS

| 6,080,401 | A | * | 6/2000 | Reddy | ............... | A61K 36/48 |
| | | | | | | 424/93.3 |
| 7,977,319 | B1 | * | 7/2011 | Levine | ............... | A21D 2/183 |
| | | | | | | 514/23 |
| 2008/0299220 | A1 | * | 12/2008 | Tamarkin | ............ | A61K 31/375 |
| | | | | | | 424/600 |
| 2017/0258861 | A1 | * | 9/2017 | Squires | ............... | A61K 9/0014 |

FOREIGN PATENT DOCUMENTS

WO    WO 2017/093961    *  6/2017

OTHER PUBLICATIONS

Aggrawal K. et al. Efficacy of a Standardized Herbal Preparation (Roidosanal(TM)) in the Treatment of Hemorrhoids. J of Ayurveda & Integrative Medicine 5(2)Apr./Jun. 2014. (Year: 2014).*

* cited by examiner

*Primary Examiner* — Ralph J Gitomer
(74) *Attorney, Agent, or Firm* — W&C IP

(57) ABSTRACT

Herbal pharmaceutical compositions for the treatment of ano-rectal diseases are provided. The compositions include *C. molmol, Gardenia* spp, *T. erecta, M. ferrea*, activated charcoal, probiotic, neem and/or curcumin, cloves, isabgol, pharmaceutical excipients, and optionally a therapeutic agent. The compositions possess properties to control inflammation by lowering levels of inflammatory cytokines and matrix metalloproteinases, prevent capillary bleeding and fragility in mammals, particularly human beings and have wound healing properties.

12 Claims, 2 Drawing Sheets

HERBAL PHARMACEUTICAL COMPOSITIONS FOR ANO-RECTAL DISEASES AND METHOD OF PREPARATION THEREOF

FIELD OF INVENTION

The present invention relates to herbal pharmaceutical compositions, more specifically, to a novel herbal composition useful for the treatment of ano-rectal diseases, including hemorrhoids, anal fissures, fistula etc. The present invention also relates to a method of preparing said pharmaceutical composition. The novel composition of the present invention possess properties to control inflammation by lowering levels of inflammatory cytokines and matrix metalloproteinases, prevent capillary bleeding and fragility in mammalians, particularly human beings and have wound healing properties.

BACKGROUND OF THE INVENTION

Hemorrhoids are one of the most common gastrointestinal disorders. They are known to occur in any age and can affect both sexes. The natural evolution of hemorrhoids is benign in nature, but they tend to get worse over time. Hemorrhoids can be caused by a variety of factors including hormones, genes, inflammation, infection, constipation, exercise, vascular stasis, diet, strain, physical stance in defecation, loss of connective tissue elasticity with age etc. The term haemorrhoid (or piles) is used to describe the enlargement of the venous tissues of the anal region, which becomes inflamed or prolapsed. Hemorrhoids can be treated through reduction of inflammation and pain, haemostasis, wound healing and protection of vascular walls. Thus, an effective treatment of acute hemorrhoidal attacks should not only provide relief as early as 4-5 days after initiation of the treatment, but also reduce the recurrence of such attacks.

The anal canal consists of three fibrovascular cushions that are supported within the anal canal by a connective tissue framework, which is important in providing a watertight seal to the anus. Hemorrhoids result from the hypertrophy of the hemorrhoidal plexus and pathological changes in the anal cushions. The degenerative effects of aging and regular straining during bowel movements may weaken the supporting tissues, producing a shearing force on the cushions, causing their descent and prolapse. The prolapsed cushions impair venous return, resulting in engorgement that may be further exacerbated by chronic straining during defecation, inadequate fiber intake, and conditions such as pregnancy, that raise intra-abdominal pressure. Bleeding from the engorged prolapsed hemorrhoid occurs as a result of localized mucosal trauma or inflammation, which damages the underlying blood vessels. The anal cushions of patients with hemorrhoids show significant pathological changes like abnormal venous dilatation, vascular thrombosis, degenerative process in the collagen fibers and fibroelastic tissues, distortion and rupture of the anal subepithelial muscle. The symptoms associated with hemorrhoids include rectal bleeding, perianal pain, discomfort, mucous discharge, perianal itching, and irritation.

Hemorrhoids are generally classified according to their position relative to the dentate line. External hemorrhoids originate below this line and become symptomatic only when thrombosed. Internal hemorrhoids arise above the dentate line and are marked by bleeding and protrusion. They can be further graded according to the degree of prolapse. Internal hemorrhoids that bleed but do not prolapse are designated as Grade I hemorrhoids; those that prolapse and reduce spontaneously (with or without bleeding) are second grade hemorrhoids; prolapsed hemorrhoids requiring manual reduction are Grade III hemorrhoids; and prolapsed hemorrhoids that cannot be reduced are Grade IV hemorrhoids.

Millions of people suffer with painful hemorrhoids chronically and regularly. It is estimated that almost half of the population over the age of 50 years suffers from piles and nearly half will experience at least one hemorrhoidal episode at some point during their lives. However, although the condition is extremely common, its exact prevalence is unknown, as many people do not consult their doctor due to embarrassment. Factors which increase intra-abdominal pressure, in particular constipation, is believed to play a role in their development. Owing to the ambiguity in the cause associated with piles, it becomes very difficult to treat them effectively.

Treatment options vary based on the degree and severity of symptoms. Management of hemorrhoids may be medical (prescribing high fiber diet, antimotility agents, topical analgesics and corticosteroid creams for symptomatic relief, alternative/traditional medicine like oral flavonoids), non-operative (sclerotherapy, cryotherapy, rubber band ligation, infrared photocoagulation, etc.) or surgical (open, closed, or stapled haemorrhoidectomy). There exist several ways of dealing with and treating this condition, however there is nothing that treats all types of haemorrhoids giving complete relief to the patients. Further, the medications/pills/ointments available, offer side effects that go with any synthetic drug. Considering that treatment of piles can be quite prolonged with available remedies, these side effects cause more damage than good. Further, since the causes and the symptoms of the condition are quite varied there is a requirement of remedy that deals with all discomforts and problems associated therewith. Thus, an effective treatment of acute hemorrhoidal attacks should not only provide relief as early as 5-7 days after initiation of the treatment, but also reduce the recurrence of such attacks.

In many countries, 70-80% of the population use traditional medicine for primary health care. As per World Health Organization (WHO), 80% of about 4000 million inhabitants on this planet rely on plant medicines. Traditional healthcare systems are known to have different treatment regimens for management of hemorrhoids. Hence, it is clear from, but not limited to, the aforementioned problems, that there is a long felt need to overcome said short comings associated with the existing remedies for treating piles of any/all types. This need has been met with by the present invention.

There exist several procedures for the treatment of hemorrhoids. Existing conservative treatments typically include life style modification, such as improving anal hygiene, increasing the intake of dietary fiber and fluids in the diet, and avoiding constipation or diarrhea, sitz baths, and rest; oral medication and topical treatment. In Europe and Asia, oral vasotopic drugs are used for treating hemorrhoids. It has been reported recently that oral micronized, purified flavonoid fraction rapidly relieves hemorrhoidal bleeding.

Many over the counter topical treatment products are available for hemorrhoids, which include pads, topical ointments, creams, gels, lotions, and suppositories. These preparations may contain various ingredients such as local anesthetics, corticosteroids, vasoconstrictors, antiseptics, keratolytics, protectants (such as mineral oils, cocoa butter), astringents (ingredients that cause coagulation, such as witch hazel), and other ingredients. Topical application of corticosteroids may ameliorate local perianal inflammation, however, long term use of high-potency corticosteroid creams can cause permanent damage and thinning of the perianal skin. Local anesthetics, such as 5% lidocaine ointment, decrease permeability to sodium ions in neuronal membranes, resulting in inhibition of depolarization, blocking transmission of nerve impulses. Vasoconstrictors like phenylephrine in topical preparations may improve local symptoms but dos not treat the underlying disorder and long term use is discouraged due to local irritation of the skin. Most of these topical treatment products help the patient maintain personal hygiene, and may alleviate symptoms of pruritus and discomfort. There are no prospective randomized trials suggesting that they reduce bleeding or prolapse. Patents in the United States of America (U.S. Pat. Nos. 4,613,498, 4,626,433, 5,166,132, 5,219,880, 5,234,914 and 4,797,392) and Europe (European patents nos. 0225832 and 0513442) have been granted in respect of compositions with varying constituents, for topical application in the form of suitable and acceptable pharmaceutical carriers, such as salts, ointments, etc., with organic, inorganic or biological active agents. However, these compositions provide only temporary relief and are limited to local application and cannot be used for systemic use or oral administration.

Several nonsurgical procedures have been used to treat hemorrhoids, which function by ablation, sclerosis, or necrosis of mucosal tissues. These include rubber band ligation, sclerotherapy, and cauterization by using electrocautery, infrared radiation, or cryosurgery. Old/new ligation techniques, some using improvised devices as in WO2005039421 A1 are still being used for treatment of hemorrhoids and new ligation techniques are evolving. Patent application WO8803398 mentions about surgical dressings for such treatment. Patents in respect of surgical devices such as European patent no. 0095142 have been granted. U.S. Pat. No. 4,621,635 has been granted for the use of lasers in the treatment of hemorrhoids. The techniques of cryopharmacotherapy and electrochemical techniques for treatment of hemorrhoids have also been patented vide European patent no. 0091405 and European patent no. 0116688, respectively. However, the biggest drawbacks of the above are the involvement of medical experts beyond mere prescription of medicines and probable hospitalization. Also, some of them are physically and/or psychologically unpleasant in application for treating such diseases. Infrared coagulation uses a infrared light source to coagulate the dilated veins of the hemorrhoid. This causes the hemorrhoid to shrink since blood does not flow through the coagulated blood vessels. Its pain free but can take more treatment sessions, when compared to ligation techniques. Injection sclerotherapy involves injecting an irritating chemical into the hemorrhoid leading to inflammation and closure of veins, hence shrinking the hemorrhoid. Hemorrhoidectomy involves surgical removing of the hemorrhoid groups. This is a surgical procedure performed under anesthesia and requires at least 1-2 weeks recovery time.

When conservative medical management fails, surgeries have been used to treat severe hemorrhoids, for example, hemorrhoidectomy, doppler guided transanalhemorrhoidaldearterialization, and stapled hemorrhoidectomy. However, all surgical treatments are associated with some degree of complications, including bleeding, infection, anal strictures, and urinary retention due to the close proximity to the rectum of the nerves that supply the bladder.

Certain wound healing agents used in management of hemorrhoids provide symptomatic relief, by promoting tissue repair, reducing inflammation and encouraging wound healing (U.S. Pat. Nos. 4,160,148, 4,508,728, 4,797,392, 4,518,583 and 5,234,914). Some others like U.S. Pat. Nos. 4,518,583 and 5,234,914 contain antimicrobial agents. These compositions, however, only relieve symptoms associated with inflammation, itching, redness, pain and swelling. Several compositions for the treatment of ano-rectal diseases (including hemorrhoids) are based on the anesthetic and vasoconstrictive properties of the constituents, but these provide only temporary symptomatic relief.

The information disclosed in this Background of the Invention section is only for enhancement of understanding of the general background of the invention. The approaches described herein are approaches that could be pursued, but not necessarily approaches that have been previously conceived or pursued. Therefore, unless otherwise indicated, it should not be assumed that any of the approaches described in this section qualify as prior art merely by virtue of their inclusion in this section nor should they be taken as an acknowledgement or any form of suggestion that this information is already known to a person skilled in the art.

OBJECTS OF THE INVENTION

In order to obviate the drawbacks in the state-of-art, the present invention provides herbal pharmaceutical compositions for the long-term management of ano-rectal diseases including hemorrhoids that are safe and painless to administer and have long-term effectiveness. The compositions of the present invention have improved efficacy and safety and are economical to manufacture.

One of the main objects of the present invention is to provide herbal pharmaceutical compositions.

Another object of the present invention is to provide herbal pharmaceutical synergistic composition effective in the management including treatment of ano-rectal diseases, including but not limited to hemorrhoids, anal fissures, fistula etc.

Yet another object of the present invention is to provide herbal pharmaceutical compositions that reduces bleeding and accelerates wound healing in the affected hemorrhoidal tissue.

Yet another object of the present invention is to provide compositions capable of providing complete relief from the ailment ensuring non-recurrence of the ailment.

Yet another object of the present invention is to provide a novel process for the preparation of the herbal pharmaceutical compositions for the treatment of ano-rectal diseases, including hemorrhoids, anal fissures, fistula etc.

Yet another object of the present invention is to circumvent the side-effects associated with the synthetic medication available for the treatment.

SUMMARY OF THE INVENTION

Accordingly, the present invention discloses novel herbal pharmaceutical compositions obtained from medicinal plants in synergistic combination with activated charcoal and probiotic as well as other ingredients, useful for the management including treatment of ano-rectal diseases, including hemorrhoids, anal fissures, fistula etc.

The individual constituents present in the present invention are reported to have anti-inflammatory, antiseptic, antioxidant, digestive, hepatoprotective and wound healing properties. The flavonoid compounds like catechins and epicatechins present in predetermined concentrations provide anti-inflammatory, haemostatic, astringent and wound healing properties.

The inventors have further researched, and have found that flavonoids rich medicinal plants containing catechins and epicatechins along with one or more pharmaceutically acceptable carriers, pharmaceutically acceptable bases or combinations thereof, provide a synergistic composition that exhibits improved pharmacological response in comparison to existing compositions employing anthocyanidins and flavonoids from other sources.

Further, the invention also relates to the method of preparing the ingredients of the herbal pharmaceutical composition and formulating the same into a dosage form, including but not limited to, tablets, pill, capsules etc. The method of preparing the said herbal pharmaceutical composition of present invention is easy, cost effective, and less time consuming in comparison to that of existing compositions employing flavonoids that employ various extraction steps, use of polar/non T polar solvents, distillations and drying procedures. The invention can also be used as health supplements.

The commercial implications of the improved and economic processing procedure led the inventors to re-establish the pharmacological and toxicological validity of the new extract and the resultant formulation provides strikingly better results than those of the similar preparations containing flavonoids as disclosed in the prior art.

STATEMENT OF INVENTION

Figure 1:
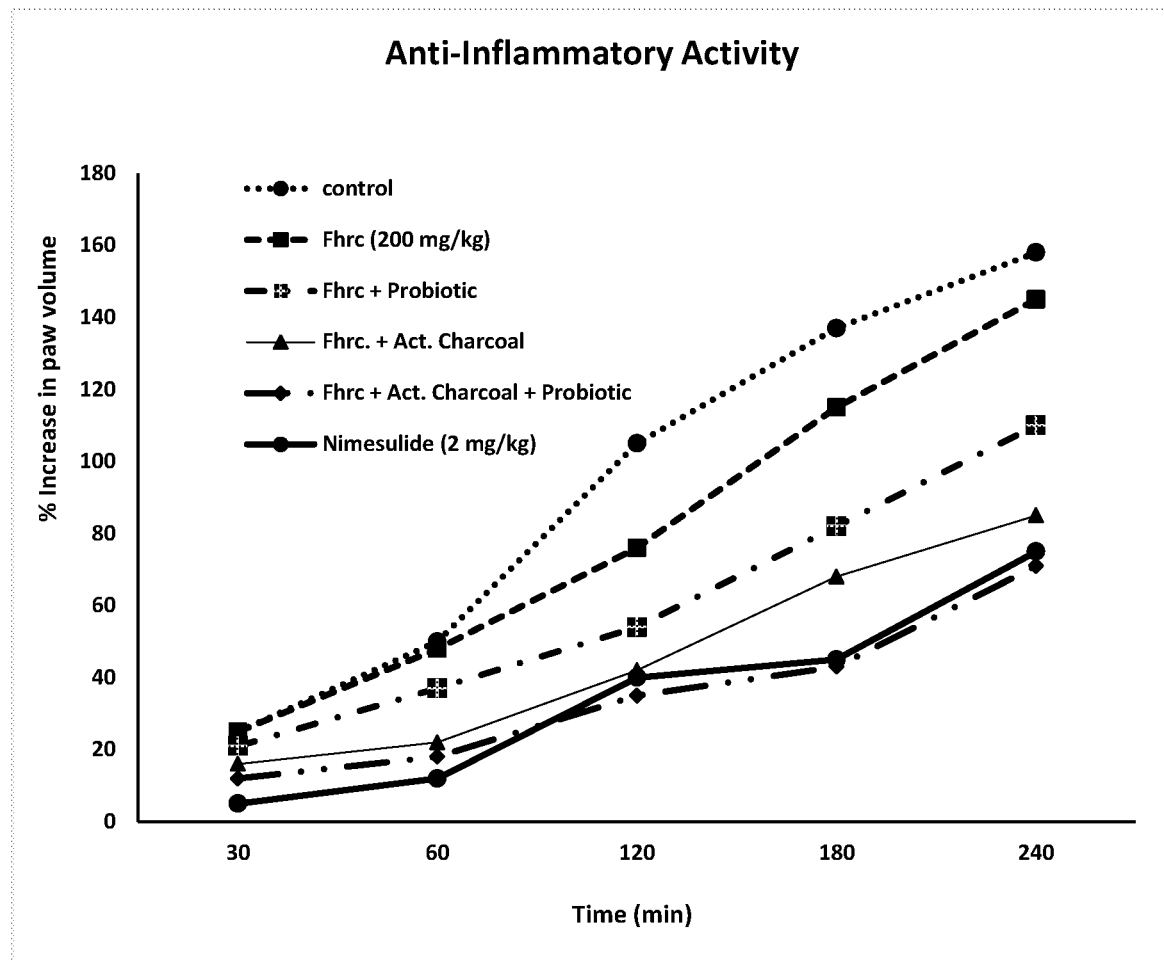
FIG. 1 depicts the Anti-inflammatory activity (Mechanism through downgrading of levels of Matrix Metalloproteinases (MMPs))

Accordingly the present invention relates to a herbal pharmaceutical compositions comprising flavonoid rich herbal component (Fhrc) in combination with activated charcoal and probiotic, and with or without therapeutic agent and pharmaceutically acceptable carrier/base to yield a synergistic composition for the treatment of ano-rectal diseases. The flavonoid rich herbal component comprises of extracts of *Commiphora molmol* either alone or in combination with at least one flavonoid rich plant(s) selected from *Gardenia* spp, *Tagateserecta* and *Mesuaferreain* such that the proportion of *C. molmol* and said flavonoid rich plant(s) is 45% to 55% by weight of *C. molmol* with balance % weight being made up of equal parts of one or more of each of the said flavonoid rich plant(s). The flavonoid rich herbal component is in the range of 8% to 25% by weight of the pharmaceutical composition, preferably in range of 10-18% by weight of the pharmaceutical composition.

The herbal pharmaceutical compositions are primarily composed of 60 to 80% *C. molmol*, either by itself or in combination with *Gardenia* spp, *T. erecta, M. ferrea* with corresponding to 10% to 18% catechins & epicatechins, 2% to 8% of activated charcoal, 10 to 25% of probiotic (corresponding to 10-50 billion CFU/g). It may optionally have Neem/*Curcumin*, clove, isabgol along with conventional excipients.

The invention also discloses process for preparing herbal pharmaceutical composition comprising the steps of cleaning and washing predetermined ratio of plant parts of *C. molmol* and said flavonoid rich plant(s), treating them at high temperatures for a few hours, combining said oxidized processed herbal powders in equal proportion to yield flavonoid rich herbal component. To this combination, activated charcoal and probiotic may be optionally added along with pharmaceutically acceptable carriers, bases or a combination thereof to yield a synergistic composition for the treatment of ano-rectal diseases.

DETAILED DESCRIPTION OF THE PREFERRED EMBODIMENT

For better understanding of the invention following terms are defined as under:

Flavonoid rich herbal component (Fhrc) include extracts of *Commiphora* molmol either alone or in combination with at least one flavonoid rich plant extract selected from *Gardenia* spp, *Tagates erecta* and *Mesua ferrea*.

Processed extracts mean extract obtained from after processing of crude extract of Flavonoid rich herbal component.

Other terms used in the specification are as described herein. In order to obviate the drawbacks of the prior art, the present invention provides a novel herbal pharmaceutical compositions obtained from medicinal plants in synergistic combination with activated charcoal and/or probiotic along with/without therapeutic agents and with/without pharmaceutically acceptable carrier/base, capable of providing relief from pain associated with ano-rectal diseases, including hemorrhoids, anal fissures, fistula etc.

The invention also significantly reduces bleeding and accelerates wound healing in the affected hemorrhoidal tissue. The invention is useful in the management of pain associated with ano-rectal diseases including treatment of lesions, other than hemorrhoids in the ano-rectal area and capable of being formulated in several types of dosage forms. More particularly, the present invention is administered orally. The invention can also be used as health supplements.

In order to obviate the drawbacks of the prior art the present herbal pharmaceutical composition have minimum or no side effects in mammals, particularly in human beings. Further, the treatment is not physically or psychologically unpleasant in its administration and/or application and hence has patient compliance.

In the following description, for the purposes of explanation, numerous specific details are set forth in order to provide a thorough understanding of the present invention. It is apparent, however, that the present invention is not limited to the embodiments described in the invention.

Various techniques are encompassed for providing an anti-haemorrhoidal herbal pharmaceutical composition for effective treatment of ano-rectal diseases including haemorrhoids of all stages and conditions and its method of preparation.

The invention encompasses anti-haemorrhoidal herbal pharmaceutical composition comprising flavonoid rich herbal component in combination with predetermined quantities each of activated charcoal and probiotic, and at least one therapeutic agent with pharmaceutically acceptable carrier/base to yield a synergistic composition for the treatment of ano-rectal diseases.

The flavonoid rich herbal component mentioned in this specification comprises of 60% to 80% by weight of processed plant plants of *C. molmol, Gardenia* spp, *T. erecta* and *M. ferrea* providing 10% to 18% of catechins and epicatechins, catechins & epicatechins)

This invention also discloses flavonoid rich herbal component in combination with activated charcoal and probiotics with/without therapeutic agents and with/without pharmaceutically acceptable carrier(s) or base in a desired dosage form, preferably as tablet/capsules/pills using conventional formulation techniques.

This invention also discloses flavonoid rich herbal component in combination with only activated charcoal with/without therapeutic agents and with/without pharmaceutically acceptable carrier(s) or base in a desired dosage form, preferably as tablet/capsules/pills using conventional formulation techniques.

This invention also discloses flavonoid rich herbal component in combination with only probiotics with/without therapeutic agents and with/without pharmaceutically acceptable carrier(s) or base in a desired dosage form, preferably as tablet/capsules/pills using conventional formulation techniques.

Of at least one plant with pharmaceutically acceptable carrier(s)/base(s). One or more of the plants are selected from *Gardenia* spp, *Tagateserecta* (Marigold), *Mesuaferrea* and *Commiphora molmol* (myrrh), and used in the composition either by itself or in various combinations. The present invention further comprises of neem (*Azadirachtaindica*) and/or *curcumin* and/or cloves (*Syzygiumaromaticum*) and/or activated charcoal and/or probiotics and/or Isabgol (*Psyllium* husk), either alone or in various combinations.

The invention also relates to the method of preparing the ingredients of the herbal pharmaceutical composition and formulating the same into a dosage form, including but not limited to, tablets, pill, capsules etc. The present composition provides relief by stimulating the digestion process, preventing constipation, relaxing the muscles, reducing inflammation, decreasing risks associated with the complications and relieving the patient of the pain and bleeding associated therewith, thereby helping the patient to lead a normal life.

In a preferred embodiment, the herbal pharmaceutical composition comprises of the gum resin of *Commiphora molmolin* a concentration range of 45%-55% for reducing inflammation and for providing relief against digestive problems. Rest of the herbal mixture of the composition comprises of the following in almost equal parts: the essential oil of the oleo gum resin of *Gardenia* spp., which is a CNS depressant and anticonvulsant with central muscle relaxant properties, thereby providing relief to the exerted and inflamed anal tissues and sphincter muscles; and the inflorescence of *Tagateserecta* or marigold used for its effectiveness in handling digestive tract problems and wound healing properties; the inflorescence of *Mesuaferrea* is used for relieving discomforts associated with constipation and other digestive issues.

In an another embodiment, the present invention, in addition to said herbal composition, further comprises of neem and/or *curcumin* in the range of 1% to 3% for detoxifying effect, and cloves in the range of 0.5% to 2% for their anodyne effect (painkiller), carminative effect and warming tendency in stomach, thereby acting as a digestive remedy. The mixture also contains activated charcoal in the range of 2% to 8% for toxin adsorption and probiotic in the range of 10% to 25% comprising of specific strains of bacteria which are known to have digestive properties and relieve symptoms of constipation.

In an another preferred embodiment the probiotic contains one or a combination of the strains of bacteria like *Lactobacillus* spp. (*L. acidophilus, L. breve, L. bulgaricus, L. casei, L. crispatus, Lactobacillus delbrueckii, L. fermentum, L. gasseri, L. helveticus, Lactobacillus jensenii, L. paracasei, L. plantarum, L. reuteri, L. rhamnosus* etc.), *Bifidobacterium* spp. (*Badolescents, B. bifidum, B. infantis, B. lactis, B. longum*), *Bacillus* spp. (*Bacillus coagulans*), *Streptococcus* spp. (*S. thermophilus, S. salivarius*) and *Saccharomyces* spp.

In another preferred embodiment, Isabgolis added in the range of 5% to 7% to the composition for its gentle laxative and cooling properties. The Isabgol also possesses properties to absorb bacteria and other harmful toxins present in the intestine and provide proper lubrication inside the intestine wall, offering comfort during defecation.

In another preferred embodiment the composition is formulated in a dosage form, including but not limited to tablets, capsules, pills such that the formulated dosage form contains at least 10% to 18% of catechins and epicatechins. The ingredients of the present invention are standardized to pharmaceutically acceptable specifications in order to ensure reproducibility from batch to batch.

In another embodiment of the present invention, if the Proanthocyanidins/flavonoids content (total catechins and epicatechins) of the composition are more than the 25%, it is standardized by mixing with pharmaceutically acceptable carrier(s)/base(s) up to the desirable range of the contents.

In another embodiment of the invention, the composition contains additional herbs for flavour like saffron or other digestion aiding plant parts. The pharmaceutical compositions of the present invention may also contain additional therapeutic agents from other plants and/or from different pharmacological groups such as anesthetics, vasoconstrictors, protectants, counterirritants, astringents, wound healing agents, antimicrobials, keratolytics, anticholinergics or their pharmaceutically acceptable salts, used either alone or in combinations thereof.

Preferably, it is beneficial to include other wound healing and antimicrobial agents resulting in the improvement of the effectiveness of the composition. In a further embodiment, the pharmaceutical composition of the present invention further comprises pharmaceutically acceptable carrier(s)/base(s) selected from but not limited to the group comprising of diluents, disintegrants, binders, anti-adherants, glidants, anti-oxidants, buffering agents, colorants, flavoring agents, coating agents, solvents, viscosifying agents, waxes, wetting agents, emulsifying agents, solubilizers, stabilizers, buffering agents, and their like, either alone or in various combinations.

The present invention also discloses a method of preparation of said herbal composition for treatment of haemorroids. The plant parts are identified and characterized according to WHO guidelines (WHO/TRM/91.4, Programme Traditional Medicines World Health Organization Geneva, 1991) and are dried under controlled conditions of temperature and humidity and cleaned appropriately. Large pieces of one of the herbs, i.e. gum resins from *C. molmol* are broken down to small pieces and collected together in a large stainless steel tank and treated at high temperatures in the range of 320° C. to 350° C. for at least 8 hr to 10 hr. The oxidized material is ground to pass through 40 mesh sieve to obtain a greyish or yellowish brown powder. The pharmaceutically active parts from the other plants such as *Gardenia* spp, *Tagateserecta* (Marigold), *Mesuaferrea* are collected together in a large shallow stainless steel vessel and oxidized at a temperature ranging from 300° C.-350° C. for 2 hr to 4 hr. The coarse material left after burning is allowed to cool and pass through 40 mesh sieve to obtain a brownish black powder. The powders so obtained from said processing, are mixed in equal proportion in a double cone blender to give the final composition called flavonoid rich herbal component.

As mentioned elsewhere in the specification the flavonoid rich herbal component comprises of 60% to 80% by weight of processed plant plants of *C. molmol, Gardenia* spp, *T. erecta* and *M. ferrea* providing 10% to 18% of catechins and epicatechins.

This flavonoid rich herbal component is then formulated with activated charcoal and probiotics with therapeutic agents and pharmaceutically acceptable carrier(s) or base in a desired dosage form, preferably as tablet/capsules/pills using conventional formulation techniques.

This flavonoid rich herbal component may also be formulated with activated charcoal and probiotics with/without therapeutic agents and with/without pharmaceutically acceptable carrier(s) or base in a desired dosage form, preferably as tablet/capsules/pills using conventional formulation techniques.

This flavonoid rich herbal component may also be formulated with only activated charcoal with/without therapeutic agents and with/without pharmaceutically acceptable carrier(s) or base in a desired dosage form, preferably as tablet/capsules/pills using conventional formulation techniques.

This flavonoid rich herbal component may also be formulated with only probiotics with/without therapeutic agents and with/without pharmaceutically acceptable carrier(s) or base in a desired dosage form, preferably as tablet/capsules/pills using conventional formulation techniques.

Although the present invention has been described in considerable detail with reference to certain preferred embodiments and examples thereof, other embodiments and equivalents are possible. Even though numerous characteristics and advantages of the present invention have been set forth in the foregoing description, together with functional and procedural details, the disclosure is illustrative only, and changes may be made in detail, especially in terms of the procedural steps within the principles of the invention to the full extent indicated by the broad general meaning of the terms. Thus various modifications are possible of the presently disclosed system and process without deviating from the intended scope and spirit of the present invention. Accordingly, in one embodiment, such modifications of the presently disclosed system and method are included in the scope of the present invention.

Evaluation of Pharmacological Activity of the Invention

Antihemorrhoidal Activity

In a pilot, active controlled, open-labeled multicentre study, 73 patients with proctoscopy proven hemorrhoids (Grade I to III) were randomly assigned to receive either invention (Gr R; n=37) or Daflon® 500 mg (Gr D; n=36), for 15 days, at three centers in India. Assessment of hemorrhoidal symptoms was carried out in all patients at different time points. Intent-to-treat analysis is performed for both primary and secondary endpoints. Baseline characteristics were comparable between the two groups. Both products were found to be equally effective in improving the anorectal conditions in Grade I and Grade II hemorrhoids; however, Roidosanal® demonstrated better efficacy in patients with Grade III hemorrhoids. Hemorrhoids associated symptoms like bleeding, pain, etc., improved in both groups, although intergroup comparisons were comparable.

[Aggrawal K, Satija N, Dasgupta G, Dasgupta P, Nain P, Sahu A R. Efficacy of a standardized herbal preparation (Roidosanal(®)) in the treatment of hemorrhoids: A randomized, controlled, open-label multicentre study. J Ayurveda Integr Med. 2014 April; 5(2):117-24. doi: 10.4103/0975-9476.131732. PubMed PMID: 24948863]

Anti-Inflammatory Activity

Carrageenan (1% w/v) induced paw oedema (Winter et al., 1962) in control group, indicating inflammatory response. Flavonoid rich herbal component (Fhrc) suspended in solvent (200 mg/kg, p.o.); Fhrc with Activated (Act.) Charcoal (9:1); Fhrc with 30-50 billion CFU of *L. acidophilus* and *B. longum* (1:1) (9:1); and Fhrc with Activated (Act.) Charcoal) and with 30-50 billion CFU of *L. acidophilus* and *B. longum* (1:1) (8:1:1) significantly decreased carrageenan-induced increase in paw volume as compared to control rats. The onset of anti-inflammatory effect was rapid and lasted up to 4 hrs after carrageenan injection. The anti-inflammatory effect of invention in groups Fhrc with Activated (Act.) Charcoal and Fhrc with Activated (Act.) Charcoal) and with 30-50 billion CFU of *L. acidophilus* and *B. longum* were comparable to that of nimesulide (2 mg/kg, p.o.), a preferential cyclooxygenase-2 (COX-2) inhibiting NSAID. Further, a solution of Invention (2-5% w/v with Act. Charcoal (5%), applied topically on paw) significantly decreased the carrageenan—induced increase in paw volume. The topical anti-inflammatory effect of the combination was comparable to that of nimesulide (2%) at 60 min as shown in FIG. 1.

Anti-Inflammatory Activity (Mechanism Through Downgrading of Levels of Matrix Metalloproteinases (MMPs))

An open label prospective study involving 52 patients with hemorrhoids (Grade I-IV) was conducted with a span of two years between July 2014 and June 2016). The patients were randomized to receive placebo (control), Flavonoid rich herbal component (Fhrc), Fhrc with 5% Activated (Act.) Charcoal (9:1) and Fhrc with 30-50 billion CFU of *L. acidophilus* and *B. longum* (1:1) (9:1) and Fhrc with 5% Activated (Act.) Charcoal (9:1) and with 30-50 billion CFU of *L. acidophilus* and *B. longum* (1:1) (8:1:1) for 15 days. Levels of MMPs (MMP-1, MMP-3, MMP-7, MMP-8 and MMP-9) at baseline and after dosing period (on day 16) were determined by immunosorbent assay. The results showed a considerable decrease in all types of MMP-s in all active treated groups, however the results were outstanding in the group taking Fhrc with Activated (Act.) Charcoal and probiotic.

|  |  | N | $t_0$ | $t_{16}$ |
|---|---|---|---|---|
| MMP-1 | Control | 11 | 4.62 ± 0.81 | 4.89 ± 0.66 |
|  | Fhrc | 10 | 4.87 ± 0.51 | 3.79 ± 0.74 |
|  | Fhrc + Act. Charcoal | 11 | 4.68 ± 0.62 | 3.62 ± 0.51 |
|  | Fhrc + Probiotic | 10 | 4.91 ± 0.76 | 3.39 ± 0.53 |
|  | Fhrc + Act. Charcoal + Probiotic | 10 | 4.85 ± 0.55 | 3.29 ± 0.32 |

-continued

| | | N | $t_0$ | $t_{16}$ |
|---|---|---|---|---|
| MMP-3 | Control | 11 | 8.32 ± 0.45 | 8.69 ± 0.95 |
| | Fhrc | 10 | 8.22 ± 1.05 | 7.98 ± 1.05 |
| | Fhrc + Act. Charcoal | 11 | 8.17 ± 0.82 | 7.89 ± 0.92 |
| | Fhrc + Probiotic | 10 | 8.16 ± 0.96 | 7.62 ± 0.31 |
| | Fhrc + Act. Charcoal + Probiotic | 10 | 8.52 ± 1.01 | 7.51 ± 0.86 |
| MMP-7 | Control | 11 | 0.36 ± 0.02 | 0.42 ± 0.03 |
| | Fhrc | 10 | 0.38 ± 0.04 | 0.37 ± 0.03 |
| | Fhrc + Act. Charcoal | 11 | 0.38 ± 0.03 | 0.36 ± 0.02 |
| | Fhrc + Probiotic | 10 | 0.39 ± 0.02 | 0.36 ± 0.03 |
| | Fhrc + Act. Charcoal + Probiotic | 10 | 0.40 ± 0.04 | 0.32 ± 0.03 |
| MMP-8 | Control | 11 | 2.32 ± 0.35 | 2.54 ± 0.29 |
| | Fhrc | 10 | 2.02 ± 0.58 | 1.72 ± 0.46 |
| | Fhrc + Act. Charcoal | 11 | 2.09 ± 0.37 | 1.69 ± 0.36 |
| | Fhrc + Probiotic | 10 | 2.12 ± 0.57 | 1.62 ± 0.49 |
| | Fhrc + Act. Charcoal + Probiotic | 10 | 2.10 ± 0.47 | 1.51 ± 0.49 |
| MMP-9 | Control | 11 | 65.22 ± 5.45 | 69.02 ± 6.15 |
| | Fhrc | 10 | 68.62 ± 6.12 | 47.21 ± 4.76 |
| | Fhrc + Act. Charcoal | 11 | 61.23 ± 5.49 | 44.33 ± 4.39 |
| | Fhrc + Probiotic | 10 | 64.12 ± 6.23 | 36.12 ± 3.41 |
| | Fhrc + Act. Charcoal + Probiotic | 10 | 63.12 ± 6.35 | 31.12 ± 3.52 |

Haemostatic Activity

Figure 2:
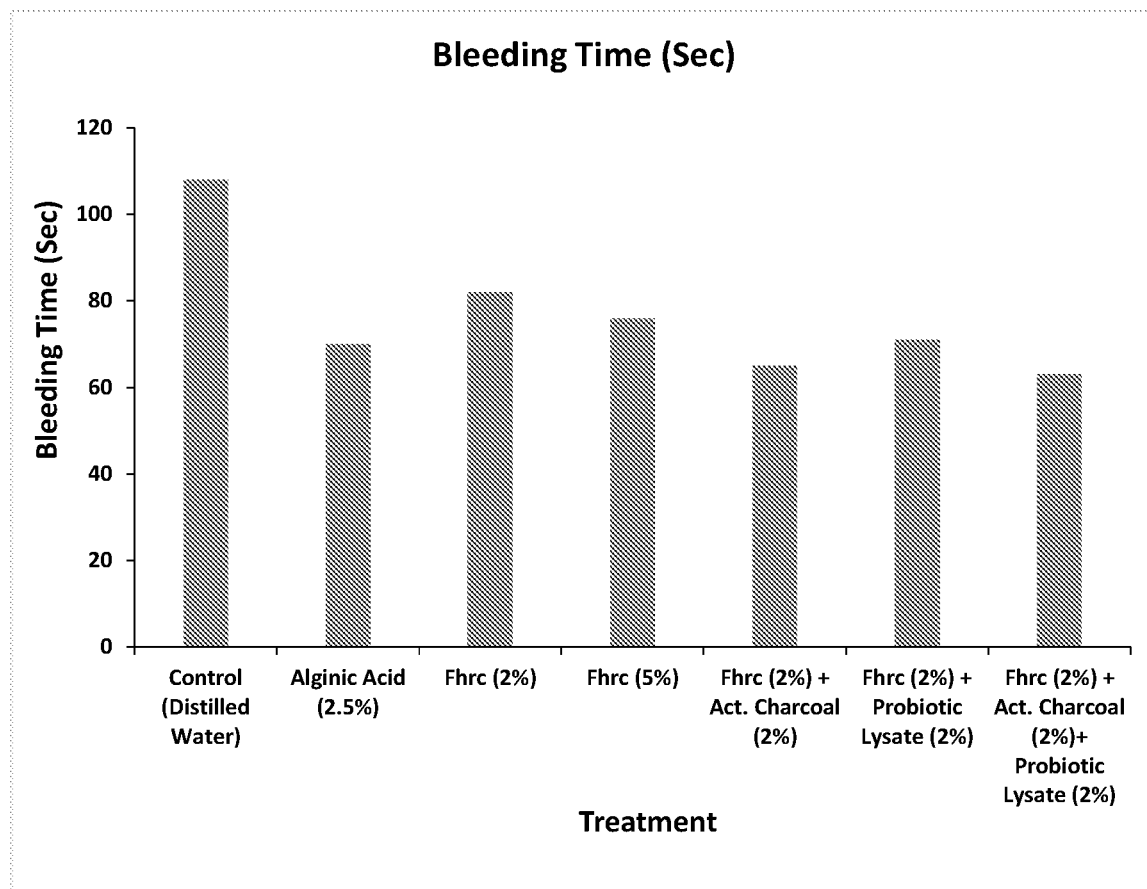
FIG. 2 depicts the comparative observation of bleeding time with variable concentrations of the invention with other ingredients.

Topical application of the invention (2% and 5%); in a formulation of Invention (2%) with Activated (Act.) charcoal (2%); in a formulation of Invention (2%) with Probiotic lysate (*L. acidophilus* and *B. longum*, 2%); and in a formulation of Invention (2%) with Activated (Act.) charcoal (2%) and Probiotic lysate (*L. acidophilus* and *B. longum*, 2%), in a liver incision model, significantly reduced the bleeding time as compared to control group (distilled water). The reduction in bleeding time observed formulation of Invention (2%) with Activated (Act.) charcoal (2%) and formulation of Invention (2%) with Probiotic lysate (*L. acidophilus* and *B. longum*, 2%) was comparable to that observed with alginic acid (2.5%), however the combination of Invention with activated charcoal demonstrated the best results as shown in FIG. 2.

Wound Healing activity

The wounds were developed by skin excision method in rats as described by Vishnu Rao et al., 1996. Topical application of the Invention (2%); in a formulation of Invention (2%) with Activated (Act.) charcoal (2%); in a formulation of Invention (2%) with Probiotic lysate (*L. acidophilus* and *B. longum*, 2%); and in a formulation of Invention (2%) with Activated (Act.) charcoal (2%) and Probiotic lysate (*L. acidophilus* and *B. longum*, 2%). Topical preparation of formulation of Invention (2%) with Activated (Act.) charcoal (2%) and formulation of Invention (2%) with Probiotic lysate (*L. acidophilus* and *B. longum*, 2%) showed significant wound healing activity in comparison to other arms on Day 4, 8, and 12 in skin excision model in rats. The results are presented in table below.

Gross examination of wounds in rats
Observation

| Time | Control | Invention Cream | Invention with Activated (Act.) charcoal | Invention (2%) with Probiotic lysate | Invention with Activated (Act.) charcoal and Probiotic Lysate |
|---|---|---|---|---|---|
| Day 4 | Bloody, raw, wet | Red, partially wet, healing started from sides | Red, partially wet, partially healed (healing from sides) | Red, partially wet, healing started from sides | Red, partially wet, partially healed (healing from sides) |
| Day 8 | partially wet, red, scar formation started | Scar formation started, partially wet | Complete Scar formed, dry | Scar formation started, partially wet | Complete Scar formed, wet at centre of wound |
| Day 12 | Scar not fully formed, not replaced with new skin | Scar formed, replacement with new skin started | Scar completely replaced with new skin, complete healing of the wound | Scar formed, replacement with new skin started | Scar completely replaced with new skin, complete healing of the wound |

Mechanism of Anti-Hemorrhoidal Activity of the Extract

Flavonoids, present in plant parts used in the invention, comprises of catechins and epicatechins, that have been reported with free radical scavenging, antioxidant, anti-inflammatory, anti-allergic, and vasodilatory activity. Proanthocyanidins including flavonoids have been shown to inhibit the enzymes hyaluronidase, elastase, and collagenase, which degrade connective tissue structures leading to increased vascular permeability. Flavonoids are often referred to as "venotonic agents", they were first described in the treatment of chronic venous insufficiency and edema. They appeared to be capable of increasing vascular tone, reducing venous capacity, decreasing capillary permeability, and facilitating lymphatic drainage as well as having anti-inflammatory effects. The flavonoids act to increase venous tone, i.e., they strengthen the walls of veins, which make them less susceptible to varicosity. In addition, these flavonoids (which, by the way, are strong antioxidants) exert a potent anti-inflammatory action that further suppresses the tendency of veins in ano-rectal region, including hemorrhoids, to become excessively permeable and fragile. Although their precise mechanism of action remains unclear, they are being used as an oral medication for hemorrhoidal treatment; sources of flavonoids are however different. A recent meta-analysis of flavonoids for hemorrhoidal treatment, including 14 randomized trials and 1514 patients, suggested that flavonoids decreased risk of bleeding by 67%, persistent pain by 65% and itching by 35%, and also reduced the recurrence rate by 47%. Some investigators have reported that MPFF can reduce rectal discomfort, pain and secondary hemorrhage following hemorrhoidectomy.

Total catechins and epicatechins in the invention possess the abovementioned activities and thus impart an easy, effective and quick resolution of symptoms and provide a long-term relief to patients.

Toxicological Studies

Acute Oral Toxicity

This study is designed to determine the acute oral toxicity of the invention to Sprague Dawleyrats. No signs of intoxication are observed in the animals treated at dose levels of 2000 mg/kg. All the animals survived throughout the study period of 14 days. Animals from test and control groups exhibited normal body weight gain on Day 7 and Day 14. Gross pathological examination did not reveal any abnormalities attributable to treatment. Lethal oral dose in the treated animals was found to be greater than 2000 mg/kg body weight.

*Salmonella* Reverse Mutation Assay

This is conducted using *S. typhimurium* strains TA 97a, TA 98, TA 100, TA 1535 and TA 102, tested against concentrations 61.72, 185.18, 555.55, 1666.67 and 5000 µg/plate using DMSO as solvent. Mean numbers of revertant colonies counted at different concentrations are comparable to that of controls. It was thus concluded that none of the concentrations induced mutations in *S. typhimurium* up to maximum concentration of 5000 µg/plate and is found not be mutagenic in the said assay.

Chromosome Aberration Test

Human lymphocyte cultures are set at 37° C. for 48 h. The cultures are exposed to 12.5 mg/culture, 6.25 mg/culture and 3.12 mg/culture of invention with and without metabolic activation for 4 h. Cultures are washed, fed with fresh medium and incubated at 37° C. for 24 h. Negative, solvent and positive controls are maintained simultaneously. After 24 h, cell cultures are harvested and observed for structural chromatid and chromosomal aberrations. Chromosome aberrations per cell and and percent cells are analyzed for statistical significance. It is observed that the invention did not induce significantly high number of chromosome aberrations at any of the concentrations. It is therefore concluded that the invention at the three concentrations (as mentioned above) did not induce chromosome aberrations in Human Lymphocyte cells Invitro up to maximum concentration of 12.5 mg/culture.

Subacute Oral Toxicity

This assay is conducted to determine the toxicity profile of the invention, when administered daily for 28 days in Sprague Dawley rats. The invention is suspended in 0.1% aqueous carboxy methyl cellulose and administered to animals at dose levels of 0 mg/kg, 250 mg/kg, 500 mg/kg and 1000 mg/kg body weight. Two additional dose levels are added to the study as 0 mg/kg (Rev.) and 1000 mg/kg (Rev.), in order to investigate the reversibility or persistence of abnormalities observed during the dosing period.

- All male and female animals from control and invention groups survived throughout the dosing period of 28 days and recovery period of 14 days.
- No signs of intoxication are observed in any of the male or female animals from any group throughout the dosing period of 28 days and recovery period of 14 days.
- Male and female animals from control and different dose groups exhibited normal weight gain and food consumption is found to be comparable throughout the dosing period of 28 days and recovery period of 14 days.
- Ophthalmological examination, hematological examination and biochemical analysis conducted prior, at end of dosing period on day 29 and at end of recovery period revealed no abnormalities attributable to treatment. Elevated alkaline phosphatase is found in female animals in 1000 mg/kg group at end of dosing period at day 29, but levels at end of post dosing recovery period on day 43, revealed no abnormalities attributable to treatment.
- Urine analysis and organ weight data at end of dosing period in week 4 and at end of the recovery period in week 6 revealed no abnormalities attributable to treatment.
- Gross pathological examination and histopathological examination on animals from different dose groups did not reveal any abnormality attributable to treatment.

Based on the findings it was concluded that the No Observed Effect Level (NOEL) of invention to Sprague Dawley rats via oral route or oral dosage form, over a period of 28 days was found to be 500 mg/kg body weight for male and female animals.

I claim:

1. A herbal pharmaceutical composition for the treatment of ano-rectal diseases, wherein said composition comprises

| Ingredient | Concentration range % |
| --- | --- |
| *Commiphora molmol, Gardenia* spp *Tagetes erecta,* and *Mesua ferrea* which provide 10% to 18% catechins & epicatechins) | 60% to 80% |
| Activated Charcoal | 2% to 8% |
| Probiotic (Corresponding to 10-50 billion CFU/g) | 10% to 25% |

-continued

| Ingredient | Concentration range % |
|---|---|
| Neem and/or Curcumin | 1% to 3% |
| Cloves | 0.5% to 2% |
| Isabgol | 5% to 7% |
| Pharmaceutical excipients | q.s | and optionally a therapeutic agent.

2. The herbal pharmaceutical composition as claimed in claim 1 wherein the catechins are in the range of 8% to 12% by weight and the epicatechins are in the range of 3% to 7% by weight.

3. The herbal pharmaceutical composition as claimed in claim 1 wherein said probiotic is selected from the group consisting of *lactobacillus* spp. (*L acidophilus, L breve, L bulgaricus, L casei, L crispatus, Lactobacillus delbrueckii, L fermentum, L gasseri, L helveticus, Lactobacillus jensenii, L paracasei, L plantarum, L reuteri, L rhamnosus* etc.), *Bifidobacterium* spp. (Badolescents, *B bifidum, B infantis, B lactis, B longum*), *Bacillus* spp. (*Bacillus coagulans*), *Streptococcus* spp. (*S thermophilus, S salivarius*) and *Saccharomyces* spp., or a combination thereof.

4. The herbal pharmaceutical composition as claimed in claim 1 wherein said therapeutic agent is selected from astringents, anaesthetics, vasoconstrictors, protectants, counterirritants, keratolytics, digestives, probiotics, wound healing agents, anti-microbial agents and combinations thereof.

5. The herbal pharmaceutical composition as claimed in claim 4, wherein said astringents are selected from the group consisting of chamomile (*Matricariachamomilla*), calendula (*Calendula officinalis*), witch hazel bark (*Hamamelis virginiana*), rose leaves (*Rosa* spp.), chestnut (*Castanea*), calamine, zinc oxide, bismuth resorcinol compound, bismuth subgallate, and tannic acid or in a combination thereof.

6. The herbal pharmaceutical composition as claimed in claim 4, wherein said anaesthetics are selected from the group consisting of caraway (*Carumcarvi*), cloves (*Syzygiumaromaticum*), turmeric (*Curcuma longa*), valerian (*Valerianaofficinalis*), benzocaine, dibucaine, tetracaine, and phenacaine or a combination thereof.

7. The herbal pharmaceutical composition as claimed in claim 4, wherein said protectants are selected from the group consisting of aluminium hydroxide gel, calamine, cocoa butter, cod or shark liver oil, starch, white petroleum, zinc oxide, vegetable or castor oil, glycols or a combination thereof.

8. The herbal pharmaceutical composition as claimed in claim 4, wherein said keratolytics are selected from the group consisting of aluminium chlorohydroxyallantoinate and resorcinol, or a combination thereof.

9. The herbal pharmaceutical composition as claimed in claim 4, wherein said digestives are selected from the group consisting of chamomile (*Matricariachamomilla*), fennel (*Foeniculumvulgare*), bael (*Aeglemarmelos*), pudina (*Menthapiperita*), or a combination thereof.

10. The herbal pharmaceutical composition as claimed in claim 4, wherein said wound healing agents are selected from the group consisting of Neem bark and fruits (*Azadirachtaindica*), Turmeric rhizomes (*Curcume longa*), tulsi leaves (*Ocimum sanctum*), arjuna bark (*Terminaliaarjuna*), aswagandha roots (*Withaniasomnifera*), sunflower seeds (*Helianthus annuus*), onion bulb (*Allium cepa*), papaya latex (*Carica papaya*), vitamin A, vitamin D, Peruvian balsam, and cod liver oil or a combination thereof.

11. The herbal pharmaceutical composition as claimed in claim 1, wherein said composition is formulated in a dosage form selected from the group consisting of a cream, ointment, solution, spray, foam, suppository, medicated pad, bandage, powder, suspension, film, oral hard gelatin capsule, soft gelatin capsule, coated tablet, uncoated tablet, modified release dosage form, liquid, lozenge, buccal or sublingual dosage form, wafer, and caplet.

12. A method of managing an ano-rectal condition selected from a hemorrhoid, fissure, crack, fistula or abscess comprising administering to a subject in need thereof a pharmaceutical composition as recited in claim 1.

* * * * *